United States Patent [19]

Kurosaka et al.

[11] 4,434,305
[45] Feb. 28, 1984

[54] PROCESS FOR PRODUCTION OF HYDROQUINONE

[75] Inventors: Nobuo Kurosaka, Yamaguchi; Makoto Yasuda, Iwakuni; Tadateru Murakami, Otake, all of Japan

[73] Assignee: Mitsui Petrochemicals Industry, Ltd., Tokyo, Japan

[21] Appl. No.: 326,277

[22] Filed: Dec. 1, 1981

[30] Foreign Application Priority Data

Dec. 5, 1980 [JP] Japan .................................. 55-170878

[51] Int. Cl.$^3$ .............................................. C07C 37/08
[52] U.S. Cl. ...................................... 568/768; 568/385
[58] Field of Search ................ 568/768, 798, 741, 385

[56] References Cited

U.S. PATENT DOCUMENTS

| | | | |
|---|---|---|---|
| 4,112,244 | 9/1978 | Nowak et al. | 568/768 |
| 4,173,623 | 1/1981 | Hashioto et al. | 568/768 |
| 4,346,203 | 1/1981 | Wirth | 568/768 |

Primary Examiner—Werren B. Lone

[57] ABSTRACT

High quality hydroquinone is produced from p-diisopropylbenzene dihydroperoxide at a high yield according to the disclosed process. The p-diisopropylbenzene dihydroperoxide is decomposed in the presence of an acid catalyst and the concentration of the hydroperoxide is maintained in the range of 0.1 to 1% by weight; the remaining hydroperoxide in the decomposition step is further subjected to an acid decomposition prior to the recovery of the formed hydroquinone product.

13 Claims, 1 Drawing Figure

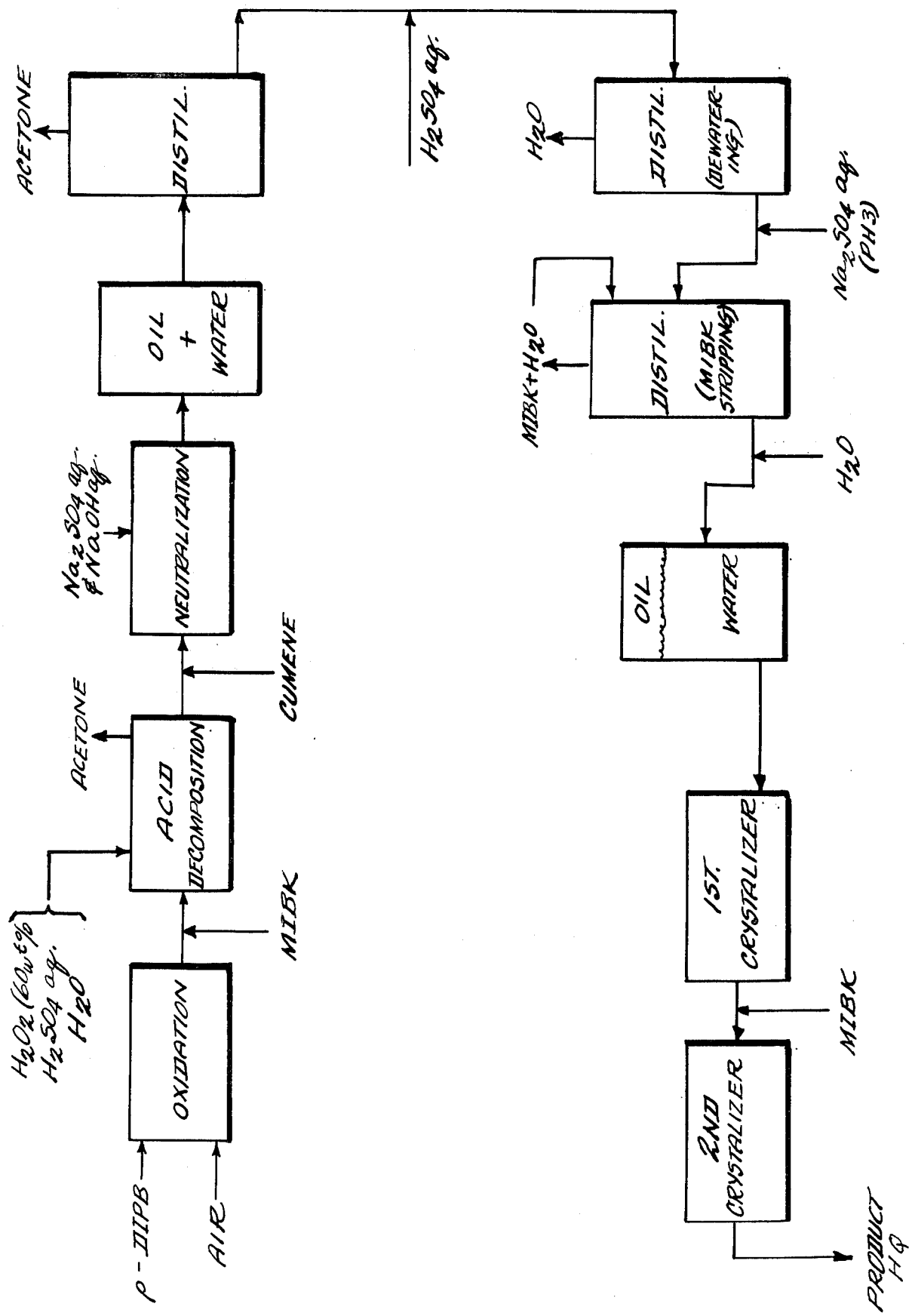

PROCESS FOR PRODUCTION OF HYDROQUINONE

BACKGROUND OF THE INVENTION

1. Field of the Invention

The present invention relates to a process for producing hydroquinone having a good color from p-diisopropylbenzene dihydroperoxide (usually referred to hereinafter as "p-DHP") at a high yield.

2. Description of the Prior Art

It has been previously known in the art that hydroquinone is produced by oxidizing, in a liquid phase, p-diisopropylbenzene (usually referred to hereinafter as "p-DIPH") and/or p-diisopropylbenzene monohydroxyperoxide (usually referred to hereinafter as "p-MHP") with molecular oxygen from p-DHP, followed by decomposition of p-DHP in the presence of an acid catalyst. However, in such an oxidation reaction, it is difficult to selectively produce only p-DHP. Furthermore, the separation of high purity p-DHP from the oxidation reaction mixture is a difficult operation and is complicated, hence expensive, to operate. For these reasons, materials other than p-DHP—including various kinds of by-products, unreacted starting materials, intermediate products and the like—are generally used as starting materials for the acid decomposition. However, when these starting materials are decomposed in the presence of an acid, it is not easy to isolate hydroquinone having a high purity at a commercially acceptable recovery yield. This is because the reaction mixture contains various components other than p-DHP including by-products derived from these components as well as by-products derived by p-DHP.

For convenience the following abbreviations are used in the following description:

p-DHP=p-diisopropylbenzene dihydroperoxide
p-DIPB=p-diisopropylbenzene
p-MHP=p-diisopropylbenzene monohydroperoxide
p-HHP=p-2-hydroxy-2-propyl-α,α-dimethylbenzylhydroperoxide Various attempts have been made to recover hydroquinone having a high purity at a good recovery yield. However, there have been few methods proposed that are convenient to operate and achieve the desired quality of the purified hydroquinone as well as the yield of the purified hydroquinone based on p-DHP. Thus, prior to the present invention there are no methods for recovering hydroquinone which satisfy all the above-mentioned requirements.

BRIEF DESCRIPTION OF THE DRAWINGS

FIG. 1 is a flow chart illustrating schematically the operational steps and procedures, including reactants and products, of Example 1.

SUMMARY OF THE INVENTION

An object of the present invention is to obviate the above-mentioned problems in the art and to provide a process for producing and recovering high quality hydroquinone at a good yield using a p-DHP as a starting material in an acid decomposition reaction in a simple and convenient operation.

Other objects and advantages of the present invention will be apparent from the description set forth below.

In accordance with the present invention, a process is provided for producing hydroquinone comprising the steps of: (1) decomposing p-diisopropylbenzene dihydroperoxide in the presence of an acid catalyst; (2) distilling the reaction mixture, after removing the acid catalyst therefrom, so that low boiling point components such as acetone, water and the like contained in the reaction mixture are removed from the reaction mixture; and, (3) recovering the thus formed hydroquinone from the distillation residue, characterized in that the decomposition is effected under conditions such that the concentration of the hydroperoxide is maintained within the range of about 0.1 through about 1% by weight and in which the remaining hydroperoxide in the decomposition step is further subjected to an acid decomposition in a distillation column during the removal of the low boiling point components or in a downstream portion of the distillation column before the recovery of the formed hydroquinone, thus decreasing the hydroperoxide concentration.

DETAILED DESCRIPTION OF THE INVENTION

As is well-known in the art, p-DHP is commercially advantageously produced by air oxidizing, in a liquid phase, p-DHP and/or p-MHP. These oxidation reaction mixtures usually contain, in addition to p-DHP, p-DIPB and p-MHP, p-2-hydroxy-2-propyl-α,α-dimethylbenzylhydroperoxide (usually referred to hereinafter as "p-HHP"), other alcohols, olefins, tar materials and the like. In the practice of the present invention these oxidation reaction mixtures can themselves be used as a starting material for the acid decomposition. Alternatively, in order to convert p-HHP contained in these mixtures to p-DHP, the above-mentioned oxidation reaction mixtures can be used after they are further oxidized by an oxidation agent such as hydrogen peroxide. Furthermore, these types of oxidation reaction mixtures may be used after a portion or all of the unreacted starting materials or by-products are separated and removed therefrom.

In the actual acid decomposition, an organic solvent capable of dissolving hydroquinone and p-DHP can be advantageously used. In view of the post-treatment operation, desirable organic solvents include (1) solvents which have a boiling point higher than that of water and which are (2) insoluble or only slightly soluble in water, and preferably (3) are those solvents which are compatible with an aromatic hydrocarbon. Examples of suitable organic solvents which satisfy these three requirements are ketones having approximately 6 through 10 carbon atoms, such as, for example, methyl isobutyl ketone, diisopropyl ketones, diisobutyl ketone and the like or, mixtures of these ketones. In addition, other organic solvents such as aromatic hydrocarbons can be used together with the above-mentioned organic solvents, as long as the desired reaction is not adversely affected.

The catalysts used in the acid decomposition of the present invention include a water-soluble acid such as sulfuric acid, phosphoric acid, perchloric acid and the like, or a solid acid such as silica-alumina, silica-magnesia, cation exchange resins and the like. The desirable catalyst is sulfuric acid, from the point of view of its low cost and the good selectivity achieved.

The content of the hydroperoxide contained in the starting material (including the solvent when a solvent is used) fed to the acid decomposition step is desirably within the range of approximately 40 through 80%, in order to maintain easy control of the reaction and for economy. As used in this description, specification and claims the content (or percentage) of the hydroperoxide is expressed in terms of percent by weight, based on the assumption that, even if the hydroperoxide is used as a mixture of various hydroperoxides, all the hydroperoxides are p-MHP when the content of the hydroperoxides are titrated with potassium iodide (the isolated iodine is back titrated with sodium thiosulfate).

The amount of the catalyst used in the acid decomposition largely depends upon the type of catalyst used and the amount of water present in the reaction mixture. As an example, when the water content in the reaction mixture is in the range of 1 through 4% by weight and when sulfuric acid is used as a catalyst, the concentration of the catalyst in the reaction mixture is desirably about 0.1 through about 2% by weight. In the case where a compound such a p-HHP, which can be coverted to p-DHP by the action of a peroxide, is contained in the starting material of the acid decomposition, a peroxide such as hydrogen peroxide may be added to the reaction mixture to achieve the desired conversion.

The reaction temperature and the period of time required for the acid decomposition reaction are not specifically limited, however the acid decomposition is advantageously carried out at a temperature of about 20° C. through about 90° C., more preferably about 50° C. through about 80° C., for a period of time of about 5 to about 60 minutes, more preferably about 15 to about 30 minutes.

In the practice of the present invention, it is important to adjust the concentration of the hydroperoxide in the reaction mixture of the acid decomposition to about 0.1 through about 1% by weight, more preferably about 0.2 through about 0.5% by weight, by appropriate selection of the above-mentioned reaction conditions. When the acid decomposition reaction is carried out until the concentration of the hydroperoxide in the reaction mixture falls below the lower limit of the above-mentioned range, not only the total yield of the hydroquinone is decreased, but also the quality of the hydroquinone is adversely affected. On the other hand, when operating under conditions where incomplete acid decomposition occurs, the amount of the remaining hydroperoxide is greater than the upper limit of the above-mentioned range which causes problems in that a dangerous abnormal reaction is likely to occur in the post-treatment operation such as distillation and also that the total yield of the hydroquinone is decreased. Thus, it is virtually necessary to operate the acid decomposition reaction at a hydroquinone concentration within the above-mentioned range.

The acid decomposition reaction can be terminated by removal of the acid catalyst. In the case where a water-soluble acid such as sulfuric acid is used, the acid catalyst can be conveniently removed from the reaction mixture by contacting the reaction mixture with an aqueous solution of a neutral salt such as, for example, an aqueous solution of sodium sulfate, potassium sulfate, sodium chloride, sodium phosphate, or ammonium sulfate; preferably an aqueous solution of a sulfate is used. Thus, the water-soluble acid is extracted from the reaction mixture to the aqueous solution layer. In order to reuse the aqueous solution of the neutral salt, a small amount of a basic compound such as sodium hydroxide can be advantageously added to the aqueous solution of the neutral salt. However, it should be noted that the use of an excess amount of the basic compound is not desirable in order to prevent a change in the properties of the hydroquinone. For this reason, the basic compound is preferably used in a manner such that, after contacting with the aqueous neutral salt solution, the oil layer containing the hydroquinone is on the acid side, for example, within the pH range of approximately 2 through 5. The term "pH of the oil layer" as used herein means a pH value of a water layer determined after the oil layer is thoroughly shaken with an equal volume of water.

In the practice of the above-mentioned extraction, in order to decrease the solubility of the hydroquinone in the water layer and to improve the separation of the water layer from the oil layer, the use of a highly concentrated aqueous solution of a neutral salt such as, for example, a concentration of approximately 5 through 30% by weight, is desirable. Furthermore, in the case where hydrocarbons such as aromatic hydrocarbons are contained in the oil layer in an amount of approximately 3 through 20% by weight, the separation is even further improved. Examples of the aromatic hydrocarbons used for this separation include toluene, xylene, ethylbenzene, cumene, cymene, mesitylene, pseudocumene, diisopropylbenzene and the like. Among these hydrocarbons, in the case where a ketone is used as an acid decomposition reaction solvent, a hydrocarbon having a boiling point higher than that of the ketone is desirably used, taking into account the separation operation in the latter step.

The reaction mixture from which the acid catalyst has been removed still contains the reaction solvent, by-products, water and the like, in addition to acetone and hydroquinone; and therefore, these components should be removed from the reaction mixture. In order to remove these components from the reaction mixture, a distillation operation can be carried out first. In the practice of the distillation, a solvent, which has a boiling point higher than that of water and which is insoluble or only slightly soluble in water but is capable of dissolving hydroquinone can advantageously is also present, since the hydroquinone can be obtained in the form of a solution after the removal of acetone and water. When a solvent is used during the acid decomposition reaction, this solvent is inevitably present in the resultant reaction mixture and, therefore, further addition of solvent is not necessary. Furthermore, the solvent should be distilled off after the removal of acetone, water and the like. In the distillation, in order to prevent decreasing the quality of the hydroquinone and maintaining tar or other high boiling point components in a dissolved form, an aromatic hydrocarbon having a boiling point higher than that of the solvent preferably is also present during the distillation. If such an aromatic hydrocarbon is used in the acid decomposition reaction or in the acid removal operation, further addition of the aromatic hydrocarbon is not necessary.

In order to remove acetone and water from the reaction mixture from which the acid catalyst has been removed, distillation can be carried out by using one distillation column, or by using two or more distillation columns acetone is first distilled off and then water is removed.

In the column bottom liquid from which water has been removed, there is present the remaining hydroperoxide which has not been completely decomposed during the acid decomposition step. The remaining hydroperoxide is further decomposed in the presence of an acid inside the distillation column from which water has been removed, or in a downstream portion of the distillation column, before the recovery of the resultant hydroquinone. This advantageously prevents the consumption of the hydroquinone during the subsequent distillation step and also prevents decreasing the quality of the hydroquinone.

The acid decomposition of the remaining hydroperoxide mentioned above can be effected in the presence of an acid catalyst similar to the acid catalyst used in the acid decomposition reaction. In the most preferred embodiment of the present invention, a small amount of a non-volatile water-soluble acid, such as sulfuric acid or phosphoric acid, is added to the feed material entering the water removal distillation column. As a result, the acid catalyst can be uniformly mixed with the feed material so that the side-reactions can be prevented, and, since the water contained in the bottom of the water removal distillation column is decreased and the acid strength is increased, the desired acid decomposition at the temperature of the distillation proceeds smoothly.

Although the amount of sulfuric acid, phosphoric acid or the like added is not specifically critical, the addition of approximately 0.001 through 0.1 parts by weight of the acid, based on 100 parts by weight of the feed materials to the distillation column, is generally sufficient. Satisfactory results are obtained when the concentration of the hydroperoxide in the column bottom liquid is decreased to one-half or less of that of the feed material, or about 0.07% or less by weight by this treatment.

The column bottom liquid thus treated is then subjected to a distillation operation in order to remove the above-mentioned solvent which is insoluble or only slightly soluble in water. In the case where the bottom temperature of the distillation column is too high during the solvent removal distillation, loss of the resultant hydroquinone occurs because a condensation reaction apparently occurs. On the other hand, if the bottom temperature of the distillation column is too low, the hydroquinone is crystallized, so that various problems including clogging of the distillation column are caused. In order to simultaneously solve these problems, the solvent may be removed by an azeotropic distillation together with water and the hydroquinone may be withdrawn in the form of an aqueous solution from the bottom of the distillation column. Oil-soluble high boiling point by-products are also withdrawn, together with aromatic hydrocarbons from the bottom of the distillation column. For this reason, the aqueous hydroquinone solution tends to be emulsified and separation becomes difficult. However, a diluted aqueous solution of a neutral salt such as sodium sulfate at a concentration, for example of 1-5% by weight, can be effectively used to obviate the above-mentioned problems.

Since the column bottom liquid is allowed to stand to separate the oil layer and the water layer, both layers can be separated in a conventional manner. In order to recover the hydroquinone from the water layer, the water layer can be concentrated to crystallize the hydroquinone. If desired, in order to increase the purity and the quality of the hydroquinone, various known operations such as an activated carbon treatment, a reducing agent treatment, a recrystallization method and the like can be used in any combination thereof. Thus, desired hydroquinone high in quality can be obtained and at a high yield.

The present invention will be further illustrated by, but is by no means limited to, the following Examples and Comparative Examples in which all parts and percentages are expressed on a weight basis unless otherwise noted.

EXAMPLE 1

The procedures of this example are illustrated schematically in the flow chart of FIG. 1. Methyl isobutyl ketone was added to the oxidation products obtained from the air oxidation of p-diisopropylbenzene. Thus, a liquid containing 23% of p-diisopropylbenzene dihydroperoxide (DHP), 10% of p-2-hydroxy-2-propyl-$\alpha,\alpha$-dimethylbenzyl hydroperoxide (HHP), 5% of p-diisopropylbenzene monohydroperoxide (MHP), 52% of methyl isobutyl ketone, 1% of water and 9% of the other products was obtained. The hydroperoxide concentration of this liquid was 64%.

The hydroperoxide concentration as used herein is based on the assumption that all the hydroperoxides are p-diisopropylbenzene monohydroperoxides. The content of the hydroperoxides is analyzed by adding a saturated potassium iodide solution to the liquid under an acetic acid acidity and, then titrating the isolated iodine with sodium thiosulfate to determine the concentration of the hydroperoxide group.

To the oxidation product which included methyl isobutyl ketone, 2.6 parts of 60% aqueous peroxide, based on 100 parts of the oxidation product, was added. Then, an acid decomposition reaction was carried out in the presence of 0.5% of sulfuric acid and 3.0% of water at a temperature of 72° C., whereby crude hydroquinone liquid including 0.35% of the unreacted hydroperoxide was obtained. The yield of the hydroquinone was 98 mol % based on the total amounts of p-DHP and p-HHP. The color, that is hue, of the resultant crude hydroquinone liquid was 0.10, which was very good, when the absorbance was determined at a wavelength of 420 nm (cell 10 mm) by using distilled water as a reference liquid.

To the resultant acid decomposition reaction mixture, sufficient cumene was added to achieve a 10% concentration. Thereafter, the resultant reaction mixture was contacted with a 20% aqueous sodium sulfate solution which contained a small amount of sodium hydroxide, then, the sulfuric acid was extracted and neutralized, whereby the pH of the oil layer of the neutralized mixture became 3.5.

After the neutralization, the oil layer was distilled at atmospheric pressure, during which acetone was distilled from the top of the column and a liquid containing 48% of methyl isobutyl ketone, 15% of hydroquinone, 14% of cumene, 14.3% of high boiling point impurities, 8% of water, 0.4% of acetone and 0.3% of the hydroperoxide was obtained as a still-bottom product. To the still-bottom liquid, 0.002 parts, based on 100 parts of the still-bottom liquid, of sulfuric acid was added, and charged to a batch distillation column, where the liquid was distilled under atmospheric pressure to remove the water from the top of the column until the water content in the bottom liquid of the distillation column was 0.7%. The hydroperoxide content of the bottom liquid of the column was 0.07%.

Then, 50 parts of a 2% aqueous sodium sulfate solution having an adjusted pH of 3 was added to 50 parts of the resultant bottom liquid of the batch distillation column and the mixture was charged to a second batch distillation column, where the methyl isobutyl ketone was distilled off, together with water, in the form of an azeotropic composition from the top of the column. All the water distilled off, together with the methyl isobutyl ketone, in the form of an azeotropic composition was recycled to the distillation column. The column bottom liquid of the methyl isobutyl ketone stripping column thus obtained was allowed to stand. Thus, the oil layer and the water layer were separated from each other. The color or hue of the water layer containing hydroquinone was 0.80, when the absorbance was determined under a wavelength of 420 nm (cell 10 mm) by using distilled water as a reference liquid. The percent hydroquinone recovered was 100% through the dewatering column and the methyl isobutyl ketone stripping column. The hydroquinone contained in the water layer thus obtained was extracted with methyl isobutyl ketone, crystallized, and recrystallized. When 5 parts of the recrystallized product was dissolved in 100 parts of 5% by volume aqueous acetic acid, the Hazen value was 5, a very acceptable value.

EXAMPLE 2

The acid decomposition reaction, neutralization and acetone stripping were carried out in the same manner as described in Example 1. Thus, a still-bottom liquid containing 48% of methyl isobutyl ketone, 15% of hydroquinone, 14% of cumene, 14.3% of high boiling point impurities, 8% of water, 0.4% of acetone and 0.3% of the hydroperoxide was obtained. To this liquid 0.01 part, based on 100 parts of the still-bottom liquid, of sulfuric acid was added and dewatered as described in Example 1 until the water content of the column bottom liquid was 0.7%. The hydroperoxide content of the column bottom liquid was 0.03%.

Thereafter, the methyl isobutyl ketone was distilled off, together with water as an azeotropic composition, in the manner described in Example 1. The color or hue of the resultant water layer including the hydroquinone was 0.75, when the absorbance was determined as described in Example 1. The recovery yield of the hydroquinone through a dewatering column and a methyl isobutyl ketone stripping column was 100%. Furthermore, the still-bottom water layer of the methyl isobutyl ketone stripping column was treated as described in Example 1. The Hazen value of the resultant product was 5, which is very good.

COMPARATIVE EXAMPLE A

The acid decomposition reaction, neutralization and acetone stripping were carried out as described in Example 1. Thus, a still-bottom liquid containing 48% of methyl isobutyl ketone, 15% of hydroquinone, 14% of cumene, 14.3% of high boiling point impurities, 8% of water, 0.4% of acetone and 0.3% of the hydroperoxide was obtained. The still-bottom liquid was distilled in the manner as described in Example 1, except that the sulfuric acid was not added until the water content thereof became 0.3%; the hydroperoxide content in the column bottom liquid was 0.23%.

Thereafter, the methyl isobutyl ketone was distilled off, together with water as an azeotropic composition, as described in Example 1. The color or hue of the resultant water layer containing the hydroquinone was determined as described in Example 1. The result was 2.5, which is very poor. The recovery yield of the hydroquinone through a dewatering column and methyl isobutyl ketone stripping column was 97.5%. The Hazen value of the product obtained from the water layer containing hydroquinone as described in Example 1 was 30, which is also very poor.

COMPARATIVE EXAMPLE B

To the oxidation product of Example 1 to which methyl isobutyl ketone was added, 2.6 parts of a 60% aqueous hydrogen peroxide, based on 100 parts of the oxidation product, was added, and a further acid decomposition reaction was carried out under the conditions of 2.5% of sulfuric acid content and 1.5% of water content at a temperature of 75° C., until the content of the unreacted hydroperoxide was 0.03%. The yield of the hydroquinone, based on the total amounts of p-DHP and p-HHP, was 88 mol %, which was very low, as compared with that of Example 1. The color or hue of the resultant acid decomposition product was determined, in terms of the absorbance, as described in Example 1. The absorbance was 0.41, which is very poor. This demonstrates that complete decomposition leads to low yields.

EXAMPLE 3

To the oxidation product obtained as described in Example 1 and to which methyl isobutyl ketone was added, 2.6 parts, based on 100 parts of the oxidation product, of 60% aqueous hydrogen peroxide was added. Then the acid decomposition reaction was carried out under conditions of 0.35% sulfuric acid content and 3.0% water content at a temperature of 75%. The unreacted hydroperoxide content in the crude hydroquinone liquid was 0.78% and the yield of hydroquinone, based on the total amounts of p-DHP and p-HHP, was 97 mol %. The color or hue of the crude hydroquinone liquid determined as described in Example 1 was 0.11. The acid decomposition reaction mixture was neutralized and acetone stripped as described in Example 1, producing still-bottom liquid containing 0.55% of the hydroperoxide. To 100 parts of this liquid, 0.02 parts of sulfuric acid was added, and dewatering was carried out by distillation as described in Example 1, until the water content of the column bottom liquid became 0.4%. The hydroperoxide content in the column bottom liquid was 0.05%.

Thereafter, the methyl isobutyl ketone was distilled off together with water, as an azeotropic composition, as described in Example 1. The color or hue of the resultant water layer containing hydroquinone also was determined in a manner as described in Example 1. The result was 0.78 which is extremely good. The yield or hydroquinone through the dewatering column and the methyl isobutyl ketone stripping column was 100%. The Hazen value of the resultant product obtained from the water layer of the still-bottom liquid of the methyl isobutyl ketone stripping column as described in Example 1 was 5, which is very good.

The results of the above Examples of the invention and Comparative Examples are shown in the following Table I.

TABLE I

| No. | Crude Hydroquinone color (absorbance) | Crude Hydroquinone hydroperoxide conc. (wt %) | yield* | Acetone Bottom hydroperoxide (wt %) | H₂SO₄** | Dewatering Bottom hydroperoxide (wt %) | H₂O (wt %) | Water Solu. color (absorbance) | Product HQ Hazen | Product HQ recovery (%) |
|---|---|---|---|---|---|---|---|---|---|---|
| 1 | 0.1 | 0.35 | 98 | 0.3 | 0.002 | 0.07 | 0.7 | 0.8 | 5 | 100 |
| 2 | 0.1 | 0.35 | 98 | 0.3 | 0.01 | 0.03 | 0.7 | 0.75 | 5 | 100 |
| A | 0.1 | 0.35 | 98 | 0.3 | 0.0 | 0.23 | 0.3 | 2.5 | 30 | 97.5 |
| B | 0.41 | 0.03 | 88 | — | — | — | — | — | — | — |
| 3 | 0.11 | 0.78 | 97 | 0.55 | 0.02 | 0.05 | 0.4 | 0.78 | 5 | 100 |

*in mole percent calculated on the total amounts of p-DHP and p-HHP.
**aqueous, in parts based upon 100 parts of the bottom liquid.

What is claimed is:

1. A process for producing hydroquinone comprising the sequential steps of:
   (1) decomposing p-diisopropylbenzene dihydroperoxide in the presence of a water-soluble acid catalyst selected from sulfuric acid, phosphoric acid, and perchloric acid at a temperature of about 20° C. to about 90° C. while maintaining the hydroperoxide concentration within the range of about 0.1 to about 1% by weight;
   (2) distilling the reaction mixture, after removing the acid catalyst therefrom, whereby low boiling point components contained in the reaction mixture are removed from the reaction mixture;
   (3) further subjecting the remaining hydroperoxide from decomposition step (1) to an acid decomposition inside the distillation column, or in a downstream portion of the distillation column, and removing the low boiling point components, including water, whereby the content of the hydroperoxide is decreased; and
   (4) removing the thus formed hydroquinone from the distillation residue.

2. A process as claimed in claim 1, wherein the distillation for removing the low boiling point components is carried out in the presence of a solvent which has a boiling point higher than that of water, which is insoluble or only slightly soluble in water, and is capable of dissolving hydroquinone whereby the hydroquinone solution is recovered as a column bottom liquid and thereafter the hydroquinone solution is distilled in the presence of water in a distillation column, the solvent is recovered from the top of the column as an azeotrope with water and the hydroquinone is recovered from the bottom of the column in the form of an aqueous solution.

3. A process as claimed in claim 1 or 2, wherein the p-diisopropylbenzene dihydroperoxide is derived from the air oxidation of p-diisopropylbenzene, p-diisopropylbenzene monohydroperoxide or a mixture thereof.

4. A process as claimed in claim 1 or 2, wherein an organic solvent, which has a boiling point higher than that of water, which is insoluble or only slightly soluble in water, and is capable of dissolving hydroquinone, coexists in the hydroperoxide decomposition step in the presence of the acid catalyst.

5. A process as claimed in claim 4, wherein said organic solvent is a ketone or mixture of ketones having from 6 to 10 carbon atoms.

6. A process as claimed in claim 5, wherein said ketones are methyl isobutyl ketone, diisopropyl ketone and diisobutyl ketone.

7. A process as claimed in claim 1 or 2, wherein the content of the hydroperoxide contained in the starting material to be decomposed in the presence of the acid catalyst is 40 through 80% by weight.

8. A process as claimed in claim 1 or 2, wherein the decomposition reaction of the hydroperoxide in the presence of the acid catalyst is carried out at a temperature of about 50° to about 80° C. for about 5 to about 60 minutes.

9. A process as claimed in claim 1 or 2, wherein the concentration of the hydroperoxide is maintained in the rage of about 0.2 to about 0.5% by weight during the decomposition step.

10. A process as claimed in claim 1, wherein the amount of said acid is about 0.001 to about 0.1 part by weight, based on 100 parts by weight of the feed material to be fed to the distillation column.

11. A process for producing hydroquinone comprising the sequential steps of:
    (1) decomposing p-diisopropylbenzene dihydroperoxide in the presence of a water-soluble acid catalyst selected from sulfuric acid, phosphoric acid, and perchloric acid at a temperature of about 20° C. to about 90° C. and maintaining the concentration of the hydroperoxide in the range of about 0.1 to about 1% by weight;
    (2) distilling the reaction mixture, after removing the acid catalyst therefrom, whereby low boiling point components contained in the reaction mixture are removed from the reaction mixture in the presence of a solvent which has a boiling point higher than that of water and which is insoluble or only slightly soluble in water but is capable of dissolving hydroquinone;
    (3) further subjecting the remaining hydroperoxide from the decomposition step to an acid decomposition in the plural distillation columns during the removal of the low boiling point components and/or said solvent whereby the content of the hydroperoxide is decreased, and solvent is recovered as an azeotrope; and
    (4) recovering the thus formed hydroquinone from the distillation residue.

12. A process for producing hydroquinone comprising the sequential steps of:
    (1) decomposing p-diisopropylbenzene dihydroperoxide in the presence of sulfuric acid or phosphoric acid, and maintaining the concentration of the hydroperoxide in the range of about 0.1 to about 1% by weight;
    (2) distilling the reaction mixture at a temperature of about 20° C. to about 90° C., after removing said sulfuric acid or phosphoric acid therefrom, whereby low boiling point components contained in the reaction mixture are removed from the reaction mixture;

(3) further subjecting the remaining hydroperoxide from the decomposition step to an acid decomposition in the distillation column during the removal of the low boiling point components where by the content of the hydroperoxide is decreased; and (4) recovering the thus formed hydroquinone from the distillation residue.

13. A process as claimed in claim 11 or 12 in which the decomposition reaction is conducted at a temperature of about 50° C. to about 80° C.

* * * * *